(12) United States Patent
Keady

(10) Patent No.: US 8,229,128 B2
(45) Date of Patent: Jul. 24, 2012

(54) DEVICE FOR ACOUSTIC SEALING

(75) Inventor: John Keady, Boca Raton, FL (US)

(73) Assignee: Personics Holdings Inc., Boca Raton, FL (US)

( * ) Notice: Subject to any disclaimer, the term of this patent is extended or adjusted under 35 U.S.C. 154(b) by 623 days.

(21) Appl. No.: 12/389,753

(22) Filed: Feb. 20, 2009

(65) Prior Publication Data

US 2009/0245530 A1    Oct. 1, 2009

Related U.S. Application Data (60) Provisional application No. 61/029,935, filed on Feb. 20, 2008, provisional application No. 61/076,122, filed on Jun. 26, 2008.

(51) Int. Cl.
  *A61F 11/06* (2006.01)
  *H04R 25/00* (2006.01)
(52) U.S. Cl. .................. 381/72; 381/52; 381/322
(58) Field of Classification Search .............. 381/58, 381/72, 322, 324, 328
See application file for complete search history.

(56) References Cited

U.S. PATENT DOCUMENTS

| | | | |
|---|---|---|---|
| 2,535,258 A | 12/1950 | Bland | |
| 3,602,654 A | 8/1971 | Victoreen | |
| 4,006,796 A | 2/1977 | Coehorst | |
| 4,133,984 A * | 1/1979 | Akiyama | 381/328 |
| 4,741,344 A * | 5/1988 | Danby et al. | 600/379 |
| 4,834,211 A | 5/1989 | Bibby et al. | |
| 4,896,679 A | 1/1990 | St. Pierre | |
| 4,962,537 A | 10/1990 | Basel et al. | |
| 5,333,622 A | 8/1994 | Casali et al. | |
| 5,483,027 A | 1/1996 | Krause | |
| 5,654,530 A | 8/1997 | Sauer et al. | |
| 5,742,692 A | 4/1998 | Garcia et al. | |
| 5,853,005 A | 12/1998 | Scanlon | |
| 5,917,918 A | 6/1999 | Callahan | |
| 6,022,311 A | 2/2000 | Juneau et al. | |
| 6,094,494 A | 7/2000 | Haroldson | |
| 6,253,871 B1 | 7/2001 | Aceti | |
| 6,256,396 B1 | 7/2001 | Cushman | |
| 6,310,961 B1 | 10/2001 | Oliveira et al. | |
| 6,339,648 B1 | 1/2002 | McIntosh et al. | |
| 6,393,130 B1 | 5/2002 | Stonikas et al. | |
| 6,438,244 B1 | 8/2002 | Juneau et al. | |
| 6,513,621 B1 | 2/2003 | Deslauriers et al. | |
| 6,671,381 B1 | 12/2003 | Lux-Wellenhof | |
| 7,110,562 B1 | 9/2006 | Feeley et al. | |
| 7,130,437 B2 | 10/2006 | Stonikas et al. | |
| 7,139,404 B2 | 11/2006 | Feeley et al. | |

(Continued)

FOREIGN PATENT DOCUMENTS

WO   WO 2008/064453   6/2006

(Continued)

*Primary Examiner* — Phuc Dang
(74) *Attorney, Agent, or Firm* — RatnerPrestia (57) ABSTRACT

An expandable device (1100) can be configured to occlude an ear canal to isolate an ear canal volume from an ambient environment. The expandable device includes a support structure (1102). A membrane having a proximal end and a distal end is attached at each end around the support structure (1102) forming an expandable element (1104). The expandable element (1104) has an expanded state and an un-expanded state. The expandable element is adjacent to the support structure (1102) in the un-expanded state. The expandable element (1104) in the un-expanded state minimizes an insert profile of the expandable device (1102).

19 Claims, 6 Drawing Sheets

U.S. PATENT DOCUMENTS

| | | |
|---|---|---|
| 7,141,014 B2 | 11/2006 | Saltykov |
| 7,164,775 B2 | 1/2007 | Meyer et al. |
| 7,227,968 B2 | 6/2007 | van Halteren et al. |
| 7,362,875 B2 * | 4/2008 | Saxton et al. ............ 381/322 |
| 7,387,187 B2 | 6/2008 | Widmer et al. |
| 7,425,196 B2 | 9/2008 | Jorgensen et al. |
| 7,984,716 B2 * | 7/2011 | Purcell et al. ............ 128/865 |
| 2002/0114479 A1 | 8/2002 | McIntoch et al. |
| 2002/0136421 A1 | 9/2002 | Topholm |
| 2002/0196958 A1 | 12/2002 | Halteren et al. |
| 2006/0159298 A1 | 7/2006 | von Dombrowski et al. |
| 2007/0116319 A1 | 5/2007 | Hagberg |
| 2007/0223759 A1 | 9/2007 | Ach-Kowalewski |
| 2008/0107287 A1 | 5/2008 | Beard |
| 2008/0144871 A1 | 6/2008 | Purcell et al. |
| 2009/0173353 A1 | 7/2009 | Purcell et al. |
| 2009/0320858 A1 | 12/2009 | Purcell et al. |
| 2009/0320859 A1 | 12/2009 | Purcell et al. |

FOREIGN PATENT DOCUMENTS

| | | |
|---|---|---|
| WO | WO 2008/075221 | 6/2006 |
| WO | WO 2008/075221 | 6/2008 |

* cited by examiner

FIG. 9 semi-log plot

FIG. 10

DEVICE FOR ACOUSTIC SEALING

CROSS-REFERENCE TO RELATED APPLICATIONS

This application claims the benefit of U.S. provisional patent application No. 61/029,935 filed on Feb. 20, 2008, the entire disclosure of which is incorporated herein by reference. This application is also related to U.S. provisional patent application No. 61/076,122 filed on Jun. 26, 2008, the entire disclosure of which is incorporated herein by reference.

FIELD OF THE INVENTION

The present invention relates to devices that can be inserted into orifices and more particularly, though not exclusively, a device that can be inserted into body orifices.

BACKGROUND OF THE INVENTION

With the advent of an industrial society, people are exposed to noise pollution at greater and greater levels; both from background, such as street traffic, airplanes, construction sites and intentional exposure to high sound levels such as cell phones, MP3 players, and rock concerts. Studies show that ear damage, leading to permanent hearing impairment is not only increasing in the general population, but increasing at a significantly faster rate in younger populations.

The potential for hearing damage is a function of both the level and the duration of exposure to the sound stimulus. Studies have also indicated that hearing damage is a cumulative phenomenon. Although hearing damage due to industrial or background noise exposure is more thoroughly understood, the risk of exposing one's self to excessive noise, especially with the use of headphones has also been recently studied. Protecting the ear from ambient noise is primarily done with the use of static earplugs that attempt to shield the inner ear from excessively high decibel noise.

Devices have been developed over the years to reduce sound from entering the ear canal. These devices known as earpieces, typically fit into the ear or around the ear. For example, headphones, earbuds, behind the ear earpieces, hearing aids, headsets and other devices attenuate sound from the ambient environment and direct acoustic energy to the tympanic membrane of the ear. People typically do not have knowledge of the cumulative sound levels that they receive on a daily basis. Moreover, both short term and long term noise exposure can be a health risk. Accordingly, a system that overcomes the shortcomings in the related art would be useful.

SUMMARY OF THE INVENTION

In one embodiment, an expandable device can be configured to occlude an ear canal to isolate an ear canal volume from an ambient environment. The expandable device includes a support structure. A membrane having a proximal end and a distal end is attached at each end around the support structure forming an expandable element. The expandable element has an expanded state and an un-expanded state. The expandable element is adjacent to the support structure in the un-expanded state. The expandable element in the un-expanded state minimizes an insert profile of the expandable device.

In one embodiment, an expandable device is configured to increase the acoustic isolation of an ear canal volume. The expandable device includes a deformable element that is operatively connected to at least one portion of the support structure. The support structure has a first input port that is pneumatically coupled to the deformable element. A first side of a valve is operatively connected to the first input port by a channel. The valve is operatively connected to a flexible housing. Deforming the flexible housing opens the valve.

In one embodiment, an ear canal volume is isolated by applying a force to an external membrane of an expandable element through a medium in the expandable element. The external membrane of the expandable element contacts an ear canal wall. The force applied to the external membrane forms an acoustic seal between the external membrane and the ear canal wall. Leakage of the medium through the external membrane is reduced by placing a barrier between the membrane and the medium to maintain the acoustic seal over an extended period of time.

In one embodiment, an expandable device isolates an ear canal volume with a first balloon that has a biologically compatible first membrane. A second balloon resides within the first balloon. The second balloon is filled with a first medium that expands the first and second balloons. The first and second balloons are expanded until the first membrane of the first balloon forms an acoustic seal with the ear canal wall.

Further areas of applicability of exemplary embodiments of the present invention will become apparent from the detailed description provided hereinafter. It should be understood that the detailed description and specific examples, while indicating exemplary embodiments of the invention, are intended for purposes of illustration only and are not intended to limit the scope of the invention.

BRIEF DESCRIPTION OF THE DRAWINGS

Exemplary embodiments of present invention will become more fully understood from the detailed description and the accompanying drawings, wherein.

DETAILED DESCRIPTION OF EXEMPLARY EMBODIMENTS OF THE PRESENT INVENTION

The following description of exemplary embodiment(s) is merely illustrative in nature and is in no way intended to limit the invention, its application, or uses.

Exemplary embodiments are directed to or can be operatively used on various wired or wireless earpieces devices (e.g., earbuds, headphones, ear terminal, behind the ear devices or other acoustic devices as known by one of ordinary skill, and equivalents). For example, the earpieces can be without transducers (for a noise attenuation application) or one or more transducers (e.g. ambient sound microphone (ASM), ear canal microphone (ECM), ear canal receiver (ECR)) for monitoring/providing sound. In all of the examples illustrated and discussed herein, any specific values should be interpreted to be illustrative only and non-limiting. Thus, other examples of the exemplary embodiments could have different values.

Processes, techniques, apparatus, and materials as known by one of ordinary skill in the art may not be discussed in detail but are intended to be part of the enabling description where appropriate. For example specific materials may not be listed for achieving each of the targeted properties discussed, however one of ordinary skill would be able, without undo experimentation, to determine the materials needed given the enabling disclosure herein.

Notice that similar reference numerals and letters refer to similar items in the following figures, and thus once an item is defined in one figure, it may not be discussed or further defined in the following figures. Processes, techniques, apparatus, and materials as known by one of ordinary skill in the relevant art may not be discussed in detail but are intended to be part of the enabling description where appropriate.

Figure 1:
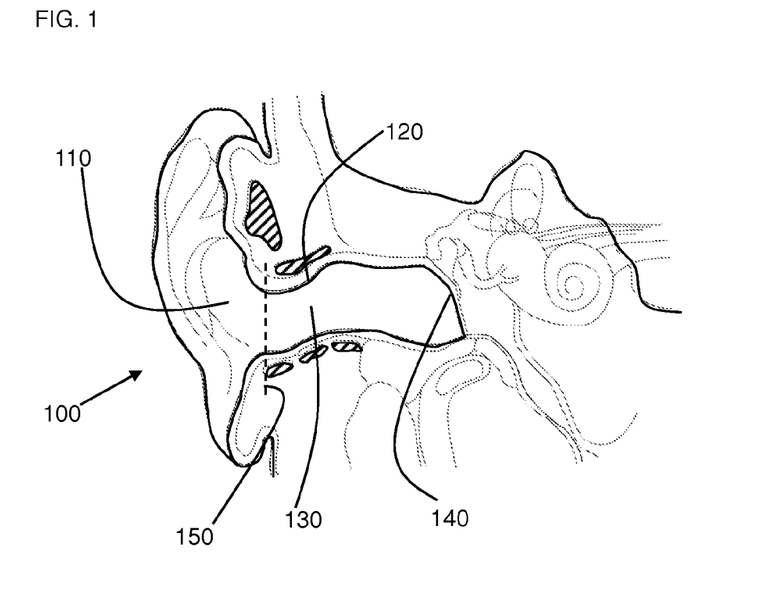
FIG. 1 illustrates general physiology of an ear.

FIG. 1 illustrates general physiology of an ear. The ear comprises a pinna 100, concha 110, ear canal wall 120, and tympanic membrane 140. Pinna 100 is an external portion of the ear. Pinna 100 is a cartilaginous region of the ear that focuses acoustic information from an ambient environment to an ear canal 130. Concha 110 is also an external portion of the ear. Concha 110 is a bowl shaped region in proximity to the ear canal opening.

A dashed line 150 indicates an opening to the ear where sound enters to be received by tympanic membrane 140. The ear canal wall 120 forms an acoustic chamber known as ear canal 130. Ear canal shapes and sizes vary substantially over the human population. Ear canal 130 terminates in tympanic membrane 140. Tympanic membrane 140 is a flexible membrane in the middle ear that couples to components of the inner ear. In general, the acoustic information resident in ear canal 130 vibrates tympanic membrane 140 that is converted to a signal (corresponding to the sound) that is provided to the auditory nerve.

Figure 2:
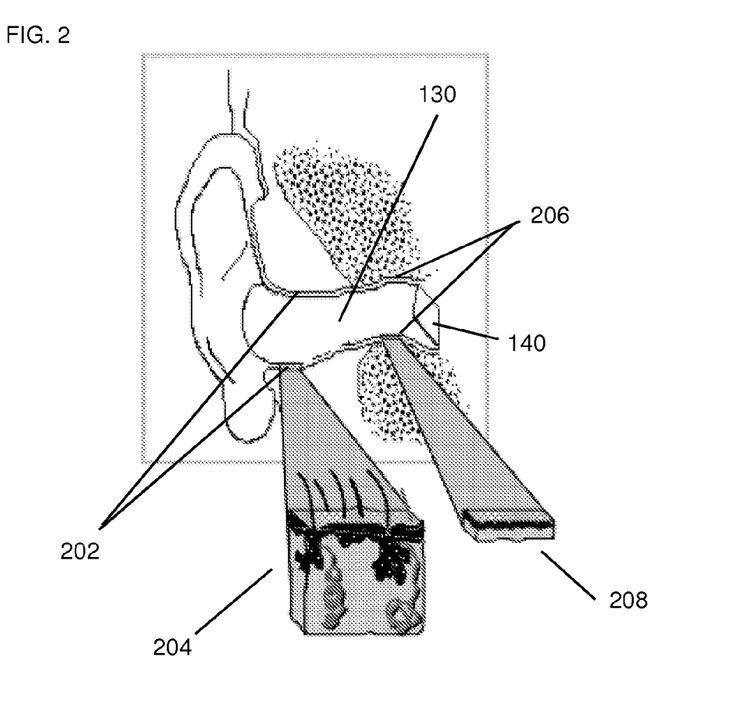
FIG. 2 illustrates a cartilaginous region and a bony region of an ear.

FIG. 2 illustrates an ear canal wall region 202 and an ear canal wall region 206 of ear canal wall 120. Ear canal wall region 206 is defined as the area where bone underlies the ear canal wall. As shown, region 206 is located in a second portion of the ear canal near the tympanic membrane 140. The skin layer of ear canal wall 120 in region 206 is sensitive to pressure. The skin layer in region 206 is approximately one tenth the thickness of the skin in ear canal wall region 202. Thus, there is not much tissue separating skin from bone. Placing an object such as an ear plug in this region can stimulate nerves due to skin being pressed against bone which can be uncomfortable and even induce significant pain. Another fact is that region 206 can radiate sound into ear canal 130 as vibrations are conducted through bone and radiated as sound into ear canal 130.

Ear canal wall region 202 is located in a first portion of ear canal 130 closest to the ear opening. Region 202 is a portion of the ear canal wall 120 that includes a layer of cartilage underlying the skin layer. Region 202 is a highly flexible region having no substantial rigid structure. A difference between regions 202 and 206 is illustrated in an exploded view of tissue 204 and tissue 208. Tissue 204 of region 202 is approximately ten times thicker than tissue 208 of region 206. The cartilage and skin of region 202 is flexible thereby making this region somewhat elastic relative to region 2056206. Thus, region 202 can be deformed when a force is applied to the area. In general, region 202 is much more insensitive to pressure (comfort/pain) than region 206. It should be noted that applying pressure to ear canal wall 120 such that ear canal wall 120 is deformed stretches and places the skin under tension.

Figure 3:
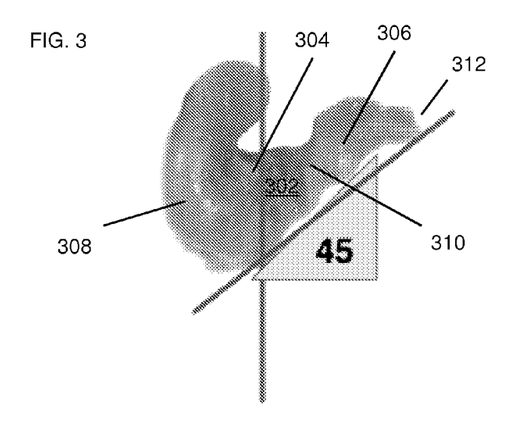
FIG. 3 is an illustration of an ear canal.

FIG. 3 is an illustration of an ear canal 302. The illustration is a mold 310 of an ear canal 302 in an orientation looking towards the face on an individual. The mold also includes concha bowl 308, which is a portion of the outer ear. Ear canal 302 has an upward tilt of approximately 45 degrees from the horizontal such that tympanic membrane 312 is above an ear canal opening. In general, an ear canal is not straight or regularly shaped. Ear canal 302 typically has a first bend 304 near the ear canal entrance and a second bend 306 that is proximate to tympanic membrane 312. It should be noted that the volume, shape, and length of ear canal 302 can vary substantially from person to person. Thus, there has been difficulty in providing a system that can effectively seal the ear, attenuate noise, mitigate occlusion effect, works under different environmental conditions, and fits a majority of the population. For example, hearing aid manufacturers have resorted to a full custom earpiece for individuals where a mold of the user's ear canal is made for forming a housing. The time and cost of this process is quite expensive.

Figure 4:
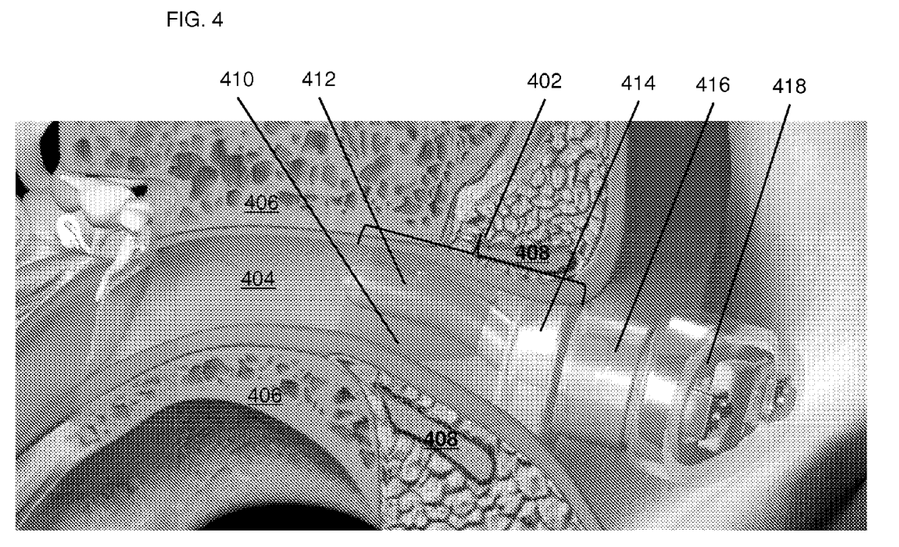
FIG. 4 is an illustration of an earpiece inserted in an ear canal in accordance with at least one exemplary embodiment.

FIG. 4 is an illustration of an earpiece inserted in an ear canal 404 in accordance with at least one exemplary embodiment. The earpiece comprises a sealing section 402 for sealing the ear, a first housing 416, and a second housing 418. Sealing section 402 creates an ear canal volume 404 that is isolated from an ambient environment. Sealing section 402 reduces sound from reaching ear canal volume 404 through two paths. The first path is the opening to the ear canal, which is sealed. The second path for sound to enter ear canal volume 404 is through bone conduction. The second path can provide significant acoustic energy to ear canal volume 404 when the wearer of the earpiece speaks. How sealing section 402 reduces sound from reaching ear canal volume 404 will be discussed in greater detail hereinbelow.

Sealing section 402 comprises a first section 410 and a second section 414. Second section 414 prevents a user of the earpiece from inserting the device too deeply into the ear canal. Second section 414 is designed to be larger than a majority of ear openings but can have a region that fits and seals the ear canal opening. Second section 414 is also referred to as a flange or a stop barrier.

First section 410 is inserted in the ear canal leaving ear canal volume 404 remaining. First section 410 contacts an ear canal wall and seals the ear canal. As shown, first section 410 can contact both a bony region 406 and a cartilaginous region 408 of the ear canal. In at least one exemplary embodiment, a surface of first section 410 in contact with the ear canal wall is under tensile stress. Furthermore, a radial force is applied to first section 410 to hold the surface against the ear canal wall. As shown, first section 410 can be formed on a stent 412 having one or more acoustic channels for providing and receiving sound.

In at least one exemplary embodiment, first housing 416 houses components of the earpiece. For example, first housing 416 can hold an instrument package comprising an ear canal receiver and an ear canal microphone. The ear canal receiver is a speaker that is coupled to an acoustic channel of stent 412 for providing sound to ear canal volume 404. Similarly, the ear canal microphone is coupled to an acoustic channel of stent 412 for receiving sound in ear canal volume 404. Furthermore, first housing 416 can house components for increasing or decreasing a volume of first section 410. For example, the volume of first section 410 is reduced to simplify removal and or insertion of sealing section 402 from the ear canal. Conversely, first section 410 is expanded for sealing the ear canal after an insertion process.

Housing 418 includes further components of the earpiece system. An ambient sound microphone can be placed in housing 418 for receiving sound in the ambient environment. Electronic components for managing audio content, modifying audio content, power management (including a battery); a/d conversion, d/a conversion, mixing, amplification, wired/wireless communication, time, and location can be included in housing 418. In general, isolating ear canal volume 404 from the ambient environment provides an opportunity to monitor sound in the ear canal. By monitoring sound received by the user of the system, an action can be taken to mitigate potential hearing damage should sound levels in the short term or over a longer period of time pose a risk to the user. Isolation from the ambient environment from a hearing perspective can result in reduced situation awareness. For example, people listening to music with an earpiece are often not cognizant of potential dangers in the ambient environment that they would normally recognize (e.g. siren or warning). The electronic components in housing 418 can be used to identify and provide sounds of importance (e.g. siren or warning) to a user when picked up by the ambient sound microphone.

Figure 5:
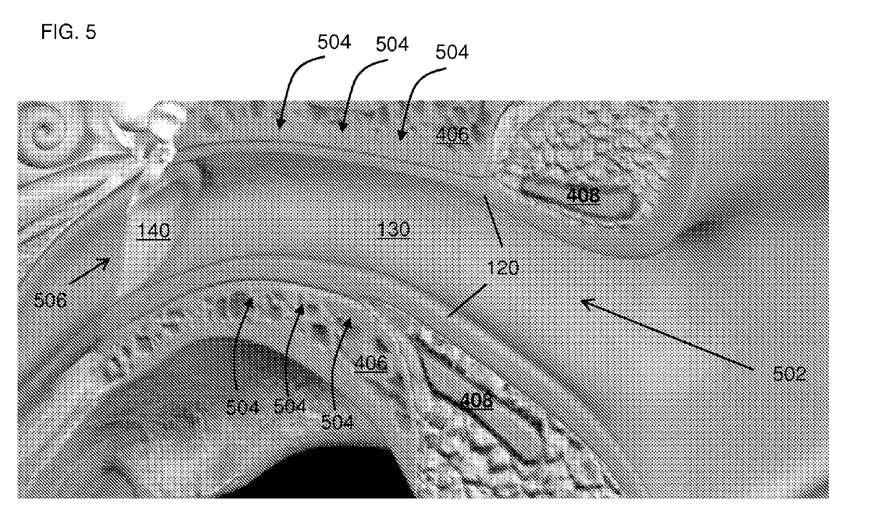
FIG. 5 is a cross sectional view an ear canal in accordance with at least one exemplary embodiment.

FIG. 5 is a cross sectional view of an ear canal in accordance with at least one exemplary embodiment. The ear canal 130 is an acoustic channel for coupling sound to tympanic membrane 140. Sound reaches ear canal 130 through several paths. The principal path 502 for sound to enter ear canal 130 coupled is through the ear canal opening in the outer ear.

Two other paths are illustrated that can provide sound into ear canal 130. Both paths are through the body and the path is not directly connected to the ambient environment. A path 504 provides sound through bone conduction. For example, sound generated when a person speaks vibrates bone adjacent to ear canal wall 120. The vibration corresponding to the speech is radiated through ear canal wall 120 by this secondary path and into ear canal 130. Similarly, a path 506 can provide sound to ear canal 130 from areas of the inner ear.

The sound provided through paths 504 and 506 is not significant under normal conditions where sound is coupled through the ear canal opening. Conversely, sealing the opening to ear canal 130 prevents sound from the ambient environment from entering. Under this condition the remaining portion of the ear canal is isolated from the ambient environment. The deleterious effect of sealing the ear canal manifests itself when a person speaks. Normally, speech radiates from the mouth and into a person's ears. Many of the high frequency components that we utter are generated by the complex interactions as the sound leaves our mouth. These high frequency components are missing when the speech is radiated through the body (e.g. bone conduction) and into ear canal 130. The sound is further modified due to resonance in the sealed ear canal volume, which amplifies (typically <500 Hz) or attenuates frequencies. The net result is that sound such as our voice is unfamiliar and can be disconcerting to some people. The sound of bone-conducted speech into the ear canal is often described as lower in frequency, boomy, and muffled. Other sounds which we normally do not hear such as chewing or teeth grinding can become much more prominent when the ear is sealed. The phenomenon of resonance boosting a low frequency signal in a sealed ear canal is known as the occlusion effect. The frequency at which the signal level is increased varies as a function of the shape, volume, and other physical attributes of the ear canal.

Figure 6:
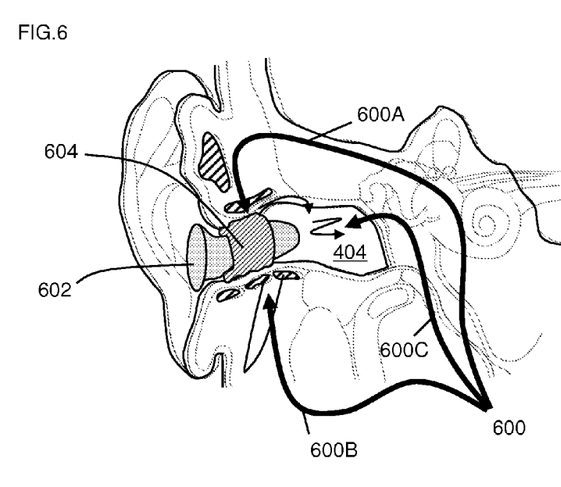
FIG. 6 illustrates a sealed or occluded ear canal in accordance with at least one exemplary embodiment.

FIG. 6 illustrates a sealed or occluded ear canal in accordance with at least one exemplary embodiment. A sealing section comprises an insertion element 602 and an expandable element 604. In a non-limiting example, insertion element 602 is a flexible element that aids in the insertion process to place expandable element 604 in an appropriate location in the ear canal. Typically, insertion element 602 is inserted centrally into the ear canal such that it does not come into contact with the ear canal wall. Insertion element 602 comprises a soft and flexible material that readily bends when contacting the ear canal wall to prevent pain or discomfort. In at least one exemplary embodiment, the length of insertion element 602 is designed so it cannot come in contact with the tympanic membrane when placed in the ear canal.

Expandable element 604 is attached to insertion element 602. Expandable element 604 is typically in a non-expanded state during insertion. In a non-limiting example, expandable element 604 is positioned on insertion element 602 such that it is positioned with its leading edge approximately half way into an average ear canal when insertion element 602 is fully inserted wherein ear canal volume 404 remains. After insertion, expandable element 602 is expanded in the ear canal and touches and forms an acoustic seal with the ear canal wall. Insertion element 602 and expandable element 604 seal an ear canal opening.

Typically, expandable element 604 contacts both the cartilaginous region and the bony region of the ear canal wall for an average user. A person with a short ear canal can have a majority or all of expandable element 604 contacting the bony region of the ear canal. Conversely, a person with a long ear canal can have a majority or all of expandable element 604 contacting the cartilaginous region of the ear canal. Ear canal volume 404 will vary from person to person. In all cases, expandable element 604 seals the ear canal and is comfortable for extended use over long periods of time. In at least one exemplary embodiment, insertion element 602 and expandable element 604 can be designed to be deeply inserted into the ear canal by increasing the length of insertion element 602. It should be also noted that insertion element 602 can include an instrument package for holding components such as transducers or electronic components.

As mentioned previously, ear canal shape and sizes can vary substantially over a large population. Insertion element 602 and expandable element 604 are designed to fit in a small ear canal opening. Expandable element 604 can then be expanded in size to seal a large or small ear canal size. Thus, insertion element 602 and expandable element 604 combine to form a component that can comfortably seal and fit a large percentage of the population. In at least one exemplary embodiment, expandable element 604 is conformal to an ear canal surface allowing a seal to be formed even if the surface is irregular in shape. A force is applied to a surface of expandable element 604 conforming and holding the surface against the ear canal wall while in use. The force is removed when the expandable element 604 is removed from the ear canal to promote easy removal.

Insertion element 602 and expandable element 604 seal an opening to the ear canal forming the ear canal volume 404 that is isolated from the ambient environment. In general, acoustic information from the ambient environment is attenuated by the sealing section. Sound can also couple to ear canal volume 404 through the body. Paths 600 illustrate areas where sound can enter. Paths 600A and 600B are bone conduction paths into ear canal volume 404. Path 600C is another path through non-bony structures such as the tympanic membrane. In at least one exemplary embodiment, the surface of expandable element 604 in contact with the ear canal wall reflects sound away from ear canal volume 404 thereby reducing the amount of sound coupled through path 600 into the ear canal.

Figure 7:
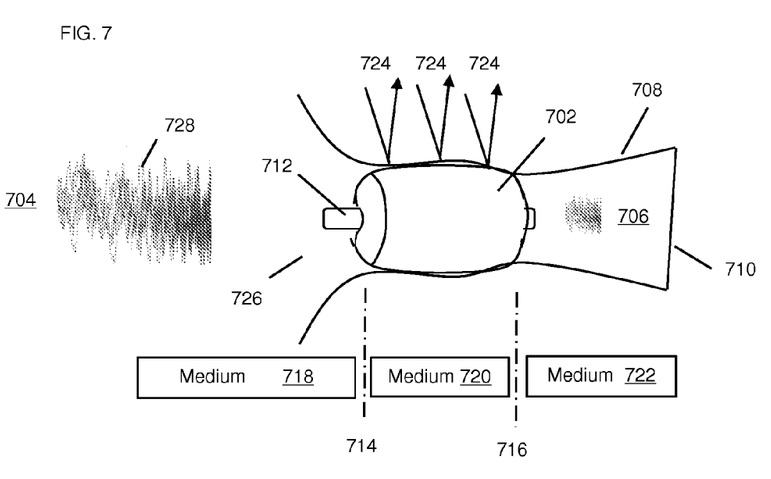
FIG. 7 is an illustration of an expandable device in an ear canal in accordance with at least one exemplary embodiment.

FIG. 7 is an illustration of an expandable device 702 in an ear canal in accordance with at least one exemplary embodiment. Expandable device 702 is inserted in an opening of the ear canal and expanded to seal the ear canal from an ambient environment 704. An ear canal volume 706 is a remaining portion of the ear canal between a distal end of expandable device 702 and a tympanic membrane 710. Expandable device 702 can be designed to take up a predetermined percentage of the total ear canal volume (from a minority to majority portion). As shown, expandable device 702 takes up approximately half of the total ear canal volume.

Painful pressure (unless released) can build up in ear canal volume 706 if expandable device 702 was inserted in an expanded state. Inserting without sealing and then expanding expandable device 702 to seal the ear canal reduces pressure from building up in ear canal volume 706. A valve (not shown) can also be provided that equalizes pressure in ear canal volume 706 and ambient environment 704 when a pressure difference occurs.

In at least one exemplary embodiment, expandable device 702 is a sealed structure that can be filled with a gas, liquid, or gel to increase volume such that the ear canal is sealed. The sealed structure can be a fixed volume or variable volume. In either a fixed volume or variable volume scenario, expandable device 702 is designed to be insertable in a small ear canal and can be expanded to fit a large ear canal thereby providing an ear canal sealing solution that covers a majority of the population. For example, a fixed volume balloon has a maximum volume designed to seal a large ear canal. The fixed volume balloon would then seal smaller ear canals requiring much less volume than the maximum volume available. Conversely, a variable volume balloon can expand or contract to the size of the ear canal from small to large. Thus, the volume of the balloon is variable. In either case, a surface of expandable device 702 is expanded to come into contact with an ear canal wall 708 of the ear canal.

There are several subjective parameters that must be met if expandable device 702 is going to achieve mainstream adoption. In general, expandable device 702 is a sealing section of an earpiece that can comprise other components (e.g. electronics, pumps, transducers, etc.) depending on the application. An earpiece is typically worn over extended periods of time. For example, eight or more hours per day. The sealing section has to be comfortable to a user. Another factor is that expandable device 702 cannot look imposing to someone placing it in their ear. In-ear devices are currently not prevalent in the market place. People may have a concern about using an in-ear device since it is unfamiliar. Thus, this negative bias can be minimized if expandable device 702 looks innocuous.

Expandable device 702 comprises a proximal surface that is directed towards ambient environment 704, a distal surface that is directed towards tympanic membrane 710, and a sidewall surface. Expandable device 702 is expanded radially until the sidewall surface contacts ear canal wall 708 and seals the ear canal. The sidewall surface of expandable device 702 is flexible and will conform to an irregular surface of ear canal wall 708 to form an acoustic seal. In at least one exemplary embodiment, the force at which the surface of expandable device 702 contacts ear canal wall 708 can be adjusted. A maximum force applied by expandable device 702 is limited to a force that will not be painful or uncomfortable to a user that has been generated by subjective measurements among a large population pool. A regulation device such as a pressure valve limits the force that can be applied.

In a non-limiting example, expandable device 702 is a balloon structure. A stent 712 includes one or more channels for providing or removing a gas, liquid, or gel to expand or contract expandable device 702. In at least one exemplary embodiment, a pump (not shown) can be used to provide or remove the medium, which fills expandable device 702. As shown, the proximal and distal surfaces are attached to stent 712 to form a sealed structure. Stent 712 can also have acoustic channels with ports at either end. The ports on the distal end of stent 712 couple to ear canal volume 706. The ports on the proximal end can couple to devices such as transducers (for providing or receiving sound) or passively coupling to ambient environment 704. Alternatively, an instrument package can also be formed in stent 712. The instrument package can include electronics, transducers, or other devices that would benefit from being in close proximity to ear canal volume 706. Wires or other interconnect would extend from a port on the proximal end of stent 712 to be coupled to other devices. The balloon surrounding the instrument package and portions of stent 712 would provide further protection from an external environment.

Modeling expandable device 702 yields a common textbook problem presented to graduate level acoustic students known as a three medium problem. Three separate volumes are identified having a boundary 714 and a boundary 716. The ambient environment 704 is a gaseous medium 718 (e.g. air). The ambient environment 704 is bounded by the proximal surface 726 of expandable device 702. The medium (e.g. gas, liquid, gel) used to expand expandable device 702 is a medium 720. The ear canal volume 706 is bounded from medium 720 by the distal surface of expandable device 702. The medium 722 in ear canal volume 706 is a gaseous medium 722 (e.g. air).

The problem addresses how much of the sound 728 in ambient environment 704 passes through expandable device 702 and into ear canal volume 706. In other words, the sound isolation properties of expandable device 702. An additional factor is that the proximal and distal surfaces of expandable device 702 as a balloon comprise a thin membrane or material. For example, in our test studies the balloon comprised a thin layer (less than 0.01 inches) of silicone or urethane material. Furthermore, the proximal and distal surfaces of the balloon would be thinner when expanded. In a non-limiting example of a gas filled variable volume balloon the material thickness of the balloon membrane can change from a thickness of 0.01 inches (uninflated) to 0.002 inches inflated when inflated to contact ear canal wall 708. In this example, the balloon pressure is greater than atmospheric and the balloon surfaces are under tensile stress. As commonly taught, the thin membrane would act as a low pass filter that would permit sound to pass from medium 718 to medium 720 and from medium 720 to medium 722. Thus, the prevailing theory would indicate that transmission loss from ambient environment 704 to ear canal volume 706 would be poor using expandable device 702.

A device as disclosed hereinabove was built and tested. Several unexpected results were measured and will be discussed in more detail hereinbelow. Tube measurements corresponding to the three medium problem using a pink noise source measured up to 40 dB attenuation in the frequency band for human hearing. Measurements were taken with expandable device 702 filled with a fluid and a gas. Attenuation differences were measurable depending on the medium (e.g. gas or liquid) placed in expandable device 702 but the difference was small in relation to the overall attenuation achieved by the device. Another unexpected result was that the attenuation was a function of the force applied to the surface of expandable element 702 on ear canal wall 708. The attenuation increased with rising force applied to the surface. For example, using a gas (air) to expand expandable device 702 saw a relationship between increasing attenuation with increasing pressure in expandable device 702.

Another unexpected result was the reduction in occlusion effect using expandable device 702. As mentioned above, the occlusion effect is noticeable when the ear is sealed and the person speaks. The sound in the ear canal is often unintelligible due to resonances in ear canal volume 706 and the predominance of low frequency sound. The low frequency sound from the voice is coupled to ear canal volume 706 through bone conduction and through other body paths. It should be noted that the normal path for hearing the human voice is blocked/attenuated by expandable device 702.

The sidewall surface of expandable device 702 is under tensile stress. For example, when expanding expandable device 702 with a gas the interior volume was pressurized to 1.2 atmospheres. The internal pressure not only applies a force pressing the sidewall surface to ear canal wall 708 but also puts the surface under tension. The sidewall surface of expandable device 702 acts as a reflective surface to reflect bone or body conducted sound away from ear canal volume 706 thereby reducing the occlusion effect. The consequence of reducing a portion of the bodily conducted sound is a legible voice signal from within the sealed ear canal cavity. Thus, enabling voice communication in a noisy environment by receiving bodily conducted voice from a sealed ear canal volume. Similarly, the proximal surface of expandable device 702 is also under tensile stress. Ambient sound 728 entering the ear canal is reflected (as shown by arrows 724) by the proximal surface. Measurements indicate that acoustic reflectivity greater than 90% can be achieved by using a thin walled membrane under tension for frequencies in the human hearing range.

Figure 8:
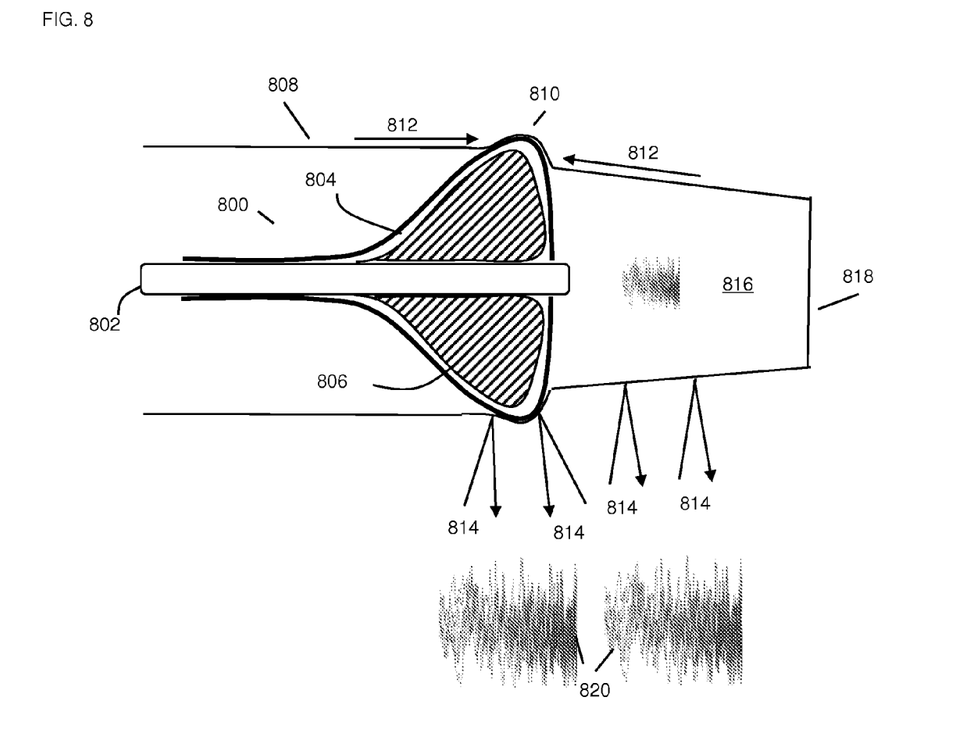
FIG. 8 is an illustration of an expanded conical shaped balloon in contact with an ear canal wall in accordance with at least one exemplary embodiment.

FIG. 8 is an illustration of an expanded conical shaped balloon 800 in contact with an ear canal wall 808 in accordance with at least one exemplary embodiment. Conical shaped balloon 800 is attached to stent 802. Stent 802 can have one or more channels as a path for providing and removing a medium 806 (for example, a gas, liquid, or gel) that respectively expands and contracts the device. Stent 802 can also have one or more acoustic channels coupled to ear canal volume 816. Conical shaped balloon 800 seals the ear canal forming an ear canal volume 816. Ear canal volume 816 is bounded by a distal surface of balloon 800, tympanic membrane 818, and ear canal wall 808.

The conical shaped balloon 800 differs from the oval shaped balloon of FIG. 7 having a reduced contact area for sealing the ear canal and forming an ear canal volume 816. It should be noted that the amount of contact area can be varied by molding the conical balloon shape to have an elongated contact area. The conical balloon shape has the contact area towards the distal end of the balloon. In a non-limiting example, conical shaped balloon 800 illustrates a tensioning effect on the skin of the ear canal when a force is applied by a balloon surface 804. The outward force applied by the balloon surface 804 in an area 810 of ear canal wall 808 deforms the skin layer. The ear canal wall skin layer is elastic and stretches since the surface area of the ear canal wall 808 has been increased by the deformation. The stretching of the ear canal wall skin layer due to deformation is indicated by arrows 812 and would occur circumferentially around ear canal wall 808. In general, the thick skin layer in the cartilaginous region would deform more than the thin skin layer in the bony region of the ear canal.

As mentioned previously, balloon 800 has a thin membrane that is under tensile stress pressed against ear canal wall 808 that seals ear canal volume 816 from the ambient environment. A portion of the sound normally conducted through bone and other internal paths (e.g. speech, chewing, etc.) into ear canal volume 816 is reflected away from the ear canal thereby reducing the occlusion effect. The amount of occlusion effect mitigation could not be entirely attributed to reflection by balloon 800. The occlusion effect is further mitigated by the process of stretching ear canal wall 808 using balloon 800. Deformation of ear canal wall 808 places the skin layer and underlying tissues under tensile stress much like the head of a drum. Similar to balloon surface 804, the stretched skin layer of ear canal wall 808 is a sound reflective surface. The occlusion effect mitigation from ear canal wall 808 is illustrated by sound 820 coming from the body and being reflected away from ear canal volume 816 as shown by arrows 814. Ear canal volume 816 is a sealed volume that has resonances that can increase the amplitude of certain frequencies while reducing others. As described above, this is most noticeable with a sealed ear canal and user speech. Measurements and subjected testing have conclusively shown that the occlusion effect is substantially decreased by reducing the amount of body-conducted sound to ear canal volume 816.

Another aspect of creating an acoustic seal in the ear canal is that it is also a watertight seal. People who are prone to ear infections or spend a lot of time in water such as a swimmer wear ear plugs. In a non-limiting example, balloon 800 can be used as an earplug for preventing a liquid from entering the ear canal. For example, prior to an event where a liquid can enter the ear, a user places a balloon 800 in each ear, inflates balloon 800 to seal the ear canal, and then engages in the event. After finishing the event the user deflates balloon 800 and removes balloon 800. Balloon 800 will have prevented the ear canal from getting wet. In at least one exemplary embodiment, balloon 800, balloon valving, and a balloon pump are housed together in a single unit for ease of use.

A problem with many earpieces having an in-ear device is maintaining the seal over an extended period of time under a wide variety of conditions. In particular, stability of the earpiece when a person is moving such as running or exercising is difficult to achieve. As disclosed above, ear canal wall 808 is slightly deformed by the internal pressure that provides a radial force that pushes surface 804 against ear canal wall 808. The deformation makes it difficult to dislodge balloon 800 even under vigorous movement. Moreover, in testing, balloon 800 is able to support a typical housing having electronics, transducers, battery, and other components for an earpiece without breaking the seal and maintaining a high level of comfort. Thus, deforming ear canal wall 808 circumferentially in the ear canal is a very stable method for holding an earpiece in place.

Figure 9:
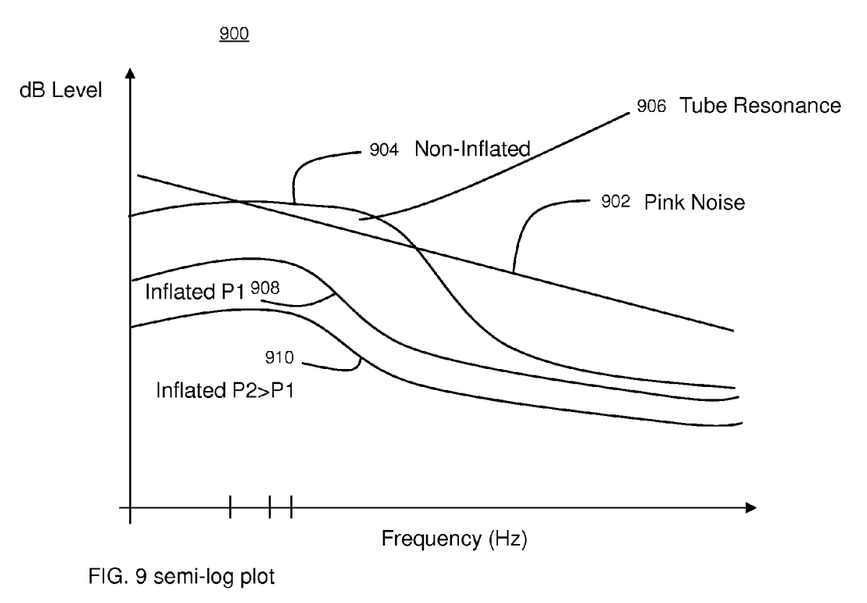
FIG. 9 is a graph illustrating sound isolation as a function of inflation of an inflatable system in accordance with at least one exemplary embodiment.

FIG. 9 is a graph 900 illustrating sound isolation as a function of inflation of an inflatable system in accordance with at least one exemplary embodiment. The inflatable system as disclosed hereinabove, seals an opening of an ear canal isolating the remaining ear canal volume from the ambient environment. The measurement is made in a flexible plastic tube having a diameter similar to an ear canal. An inflatable system is inserted in the tube forming a first region, the balloon, and a second region. In the first region of the tube, pink noise 902 is provided to a first side of the inflatable system that is measured by a microphone. In the second region (isolated by the inflatable system) measurements are taken by a second microphone. The amount of sound isolation provided by the inflatable system is the difference in the measured sound levels in the first and second regions. The tube in the second region is extended to a length where signal reflection is not a measurement issue (e.g. there is no reflected signal received by the second microphone). Additionally, the inflation medium can be a liquid, gas, gel, or other medium to increase/decrease the pressure within the inflatable system to form a seal that isolates the second region from the first region.

In at least one exemplary embodiment, the inflatable system is a gas filled balloon. The diameter of the balloon increases as it is inflated. The balloon creates an acoustic seal when the balloon surface contacts the tube wall. Raising the pressure within the balloon increases the radial force pressing the balloon surface against the tube wall.

The curve 904 represents the measurement when the inflatable system is not completely sealed. Prior to an acoustic seal being formed, a portion of pink noise 902 passes through openings coupling the first region to the second region. The measured signal in the second region will vary in intensity across the frequency band. The portion of curve 904 that is above the pink noise signal is due to resonance 906 in the second region. As shown, both the low frequency and high frequencies are attenuated in the second region.

A curve 908 represents the inflatable system at a first pressure P1 greater than or equal to a seal pressure where the inflatable system has conformed to the inside of the tube. There is a distinct drop between the sound pressure levels from the first region to the second region when the inflatable system forms an acoustic seal with the tube. This is indicated by curve 908 being less than curve 902 at all frequencies. Typically, the amount of isolation is not constant but varies over frequency. A curve 910 represents the inflatable system inflated to a second pressure P2 greater than pressure P1. Increasing the pressure in the inflatable system provides improvement of the attenuation properties of the system.

The principal of increasing and decreasing pressure can be used to enhance protection of an earpiece user. The inflatable system can be kept at the sealing value pressure (or slightly greater) under normal operating conditions to maximize comfort to the user. For example, minimum pressures can be used under moderate noise levels where the measured sound pressure levels and SPL_Dose does not indicate a potential harmful situation to the user. Furthermore, an earpiece can have circuitry for measuring sound pressure level. Upon detecting a rise in sound pressure level (e.g. greater than 1 dB) or to mitigate potential hearing damage to the user the inflatable system pressure can be increased to raise the attenuation of ambient noise thereby providing further protection. Conversely, detecting benign conditions in the ambient environment, the earpiece could lower the pressure in the inflatable system. Thus, the level of attenuation can be varied correspondingly to pressure within a range that is comfortable to the user.

Figure 10:
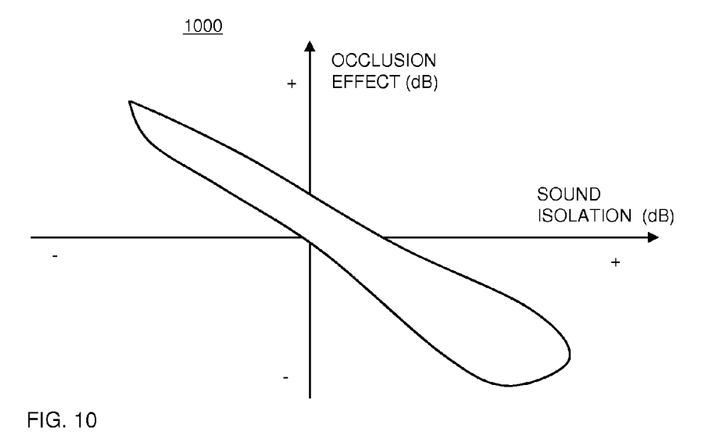
FIG. 10 is a graph of sound isolation versus occlusion effect in accordance with at least one exemplary embodiment.

FIG. 10 is a graph 1000 of sound isolation versus occlusion effect in accordance with at least one exemplary embodiment. The occlusion effect was measured for a sealed ear canal. In general, a sealing section having a surface comprising sound reflective material was held against an ear canal wall. In at least one exemplary embodiment, the sound reflective material was under tensile stress to increase the material reflectivity. The force holding the sound reflective material against the ear canal wall also deforms and stretches the elastic skin layer. The sealing section and the stretched ear canal skin layer reflect sound propagating through the body away from the ear canal.

In a non-limiting example, the sealing section is an expanding device such as a balloon. Graph 1000 shows that the occlusion effect is reduced as attenuation is increased. Conversely, the occlusion effect increases as the attenuation decreases. As disclosed above, increasing pressure of the balloon increases attenuation between the ambient environment and the ear canal. Increasing pressure also increases the tensile stress on the surface material of the balloon and further deforms and stretches the ear canal skin layer. The result of which is improved reflectivity of body-propagated sound away from the ear canal thereby reducing the occlusion effect.

Figure 11:
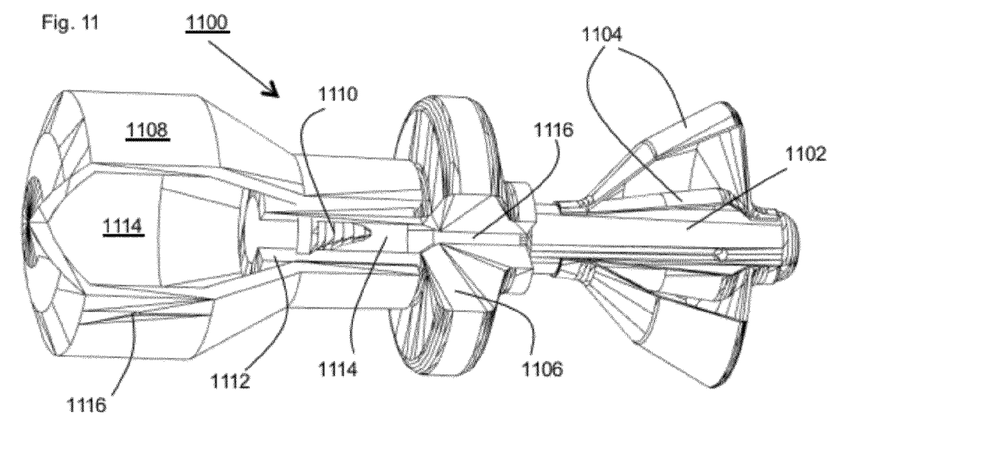
FIG. 11 is a cross-sectional view of an expandable device for occluding an ear canal in accordance with at least one exemplary embodiment.

FIG. 11 is cross-sectional view of an expandable device 1100 for occluding an ear canal in accordance with at least one exemplary embodiment. Expandable device 1100 isolates an ear canal volume from the ambient environment and reduces the occlusion effect. Expandable device 1100 comprises a deformable volume 1108, a normally closed valve 1110, a support structure 1102, and an expandable element 1104. In a non-limiting example, support structure 1102 further includes a flange 1106 also referred to as a stop barrier. Expandable element 1104 is shown in an un-expanded state and an expanded state. Expandable element 1104 comprises a membrane that is attached to support structure 1102 circumferentially at a distal and proximal end of the membrane. The membrane can be attached by adhesive, welding, or other fastening methodology. Expandable element 1104 can be a variable volume structure or a fixed volume structure. In at least one exemplary embodiment, multiple expandable elements can be formed on support structure 1102.

In at least one exemplary embodiment, expandable element 1104 is a variable volume structure having an un-expanded profile that conforms approximately to the shape of support structure 1102. As shown, the membrane of expandable element 1104 in the un-expanded state is adjacent to the major surface of support structure 1102. The membrane can be under tension where the surface is in complete contact with the surface of support structure 1102 or can have a slight gap due to stretching or loss of elasticity of the membrane. In either case, expandable device 1100 has a minimal insert profile that would be very benign to a user trying the device for the first time. In a non-limiting example, the total diameter of support structure 1102 and expandable element 1104 is less than 4 millimeters. Support structures having a diameter of less than 2.5 millimeters have been manufactured that include a plurality of channels. A similar minimal insert profile can be achieved for a fixed volume structure if the medium is completely or almost completely evacuated.

In at least one exemplary embodiment, expandable element 1104 comprises silicone or polyurethane. Other materials such as dimethylsilicone rubber, fluorosilicone, nitrile rubber, natural rubber, polyethylene, butyl rubber, polystyrene, polyethylene, nylon 6, poly(ethylene terephthalate), and Teflon can be used to form expandable element 1104. Forming support structure 1102 from the same material as expandable element 1104 can simplify the attaching process. A channel 1116 is formed in support structure 1102. Channel 1116 is a pathway for the medium to expand expandable element 1104. The medium for expanding expandable element 1104 can be a gas, liquid, or gel. Channel 1116 has a first port and a second port coupled to an interior volume of expandable element 1104.

A pumping system for expanding and contracting expanding expandable element 1104 comprises deformable volume 1108, normally closed valve 1110, and a valve housing 1112.

Deformable volume 1108 includes an opening 1118 and has an interior volume 1114 shown under quiescent conditions. Valve housing 1112 has a first port coupled to a port of deformable volume 1108 and a second port coupled to channel 1116. Normally closed valve 1110 is fitted between the first and second port in valve housing 1112. In at least one exemplary embodiment, normally closed valve 1110 is a duck-billed valve having a first port coupled to interior volume 1114 and a normally closed port coupled to channel 1116. Valve housing 1112 and normally closed valve 1110 are formed from a flexible or compressible material. Finger holds (not shown) are formed in a region of housing 1112 where the normally closed valve 1110 is located. Squeezing valve housing 1112 where the finger holds are located manually opens the duck-billed valve 1110 coupling interior volume 1114 to an interior volume of expandable element 1104.

In general, support structure 1102 is inserted in an ear canal with expandable element 1104 in an unexpanded state. Flange 1106 limits the insertion depth of expandable device 1100 into the ear canal. Flange 1106 is larger than a statistically large ear canal opening. Flange 1106 can also have a sealing element (not shown) that can seal the ear canal opening to further improve sound isolation. For example, the flange as illustrated in FIG. 4 has a flexible lip that seals the ear canal opening. This allows expandable device 1100 to be inserted without pressurizing the ear canal because the diameter of support structure 1102 is smaller than a statistically small ear canal diameter. Although shown as being straight, support structure 1102 can have a more complex shape that aids in inserting and positioning expandable element 1104 in the ear canal. As mentioned previously, the ear canal shape varies and has multiple bends.

In at least one exemplary embodiment, the medium for expanding expandable element 1104 is a gas such as air. Air enters interior volume 1114 of deformable volume 1108 through an opening 1118. Air is provided to expand expandable element 1104 by sealing opening 1118 (e.g. covering opening 1118 with a finger) and deforming deformable volume 1108. Deformation of deformable volume 1108 comprises squeezing the bulb to reduce interior volume 1114 from the quiescent state volume to a substantially smaller interior volume. Alternatively, a deformable volume 1108 can be designed to be pushed-in to reduce interior volume 1114. Reducing interior volume 1114 compresses or pressurizes the air, which forcibly opens normally closed valve 1110. A portion of the air in interior volume 1114 passes through channel 1116 and into expandable element 1104. Normally closed valve 1110 closes after passing the air. Pressure in expandable element 1104 also aids in closing and holding closed valve 1110. Releasing deformable volume 1108 while uncovering opening 1118 fills internal volume 1114 with air from the ambient environment and returns the pump to a quiescent state. The process is repeated until expandable element 1104 contacts and forms an acoustic seal with the ear canal wall thereby isolating an ear canal volume from the ambient environment.

In at least one exemplary embodiment, a pressure release valve (not shown) is fitted in valve housing 1112. The pressure release valve opens above a predetermined pressure and is normally closed. The pressure release valve has first port coupled to channel 1116 and a second port coupled to the ambient environment to release gas. The pressure release valve prevents expandable element 1104 from being pressurized to a level that could cause pain to the user of expandable device 1100 or damage expandable element 1104.

Expandable element 1104 is placed in the un-expanded state when inserting or removing expandable device 1100 from the ear canal. Removing expandable element in an expanded state could pull on the tympanic membrane (vacuum due to acoustic seal) causing pain or possibly rupturing the delicate structure. Typically, expandable element 1104 operates in a range of approximately 1-1.3 atmospheres to provide comfort, attenuation, and a reduction in the occlusion effect. Subjective testing has shown that people with sensitive ear canals feel discomfort or pain when expandable device 1104 is pressurized over 1.3 atmospheres. The pressure release valve typically opens before the pressure in expandable device 1104 reaches 1.3 atmospheres with a safe margin to minimize any discomfort to a statistically large segment of the population. Expandable element 1104 is placed in the un-expanded state as disclosed hereinabove by squeezing valve housing 1112 in a region where normally closed valve 1110 resides thereby manually opening the duck-bill. In at least one exemplary embodiment, the membrane of a variable volume structure is under tensile stress when expanded and returns to the lowest stress condition (e.g. the un-expanded state with the membrane adjacent to the surface of support structure 1102) thereby forcibly evacuating an interior volume of expandable element 1104. Air from the interior volume of expandable element 1104 passes through channel 1116, normally closed valve 1110, interior volume 1114, and into the ambient environment through opening 1118. Once placed in the un-expanded state, expandable device 1100 can be removed from the ear.

Figure 12:
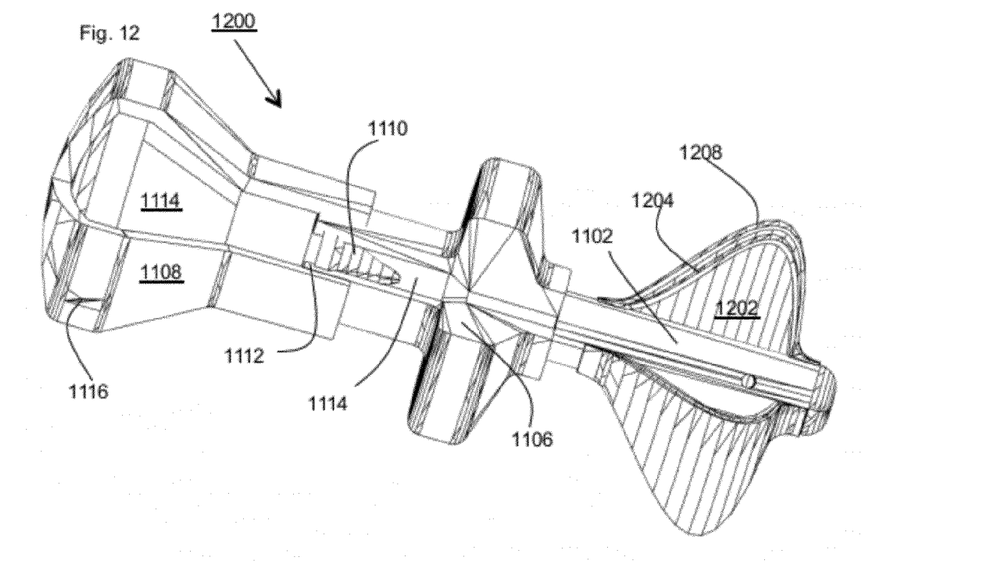
FIG. 12 is a cross-sectional view of an expandable device for occluding an ear canal in accordance with an exemplary embodiment.

FIG. 12 is a cross-sectional view of an expandable device 1200 that occludes an ear canal in accordance with an exemplary embodiment. Expandable device 1200 includes deformable volume 1108, opening 1118, valve-housing 1112, normally closed valve 1110, channel 1116, flange 1106, and support structure 1102 of FIG. 11. Thus, the pumping process, insertion process, and removal process operates similarly to that described above.

In general, a membrane material for a balloon 1206 to occlude the ear canal that is suitable for comfort and biocompatibility reasons (e.g. soft, does not scratch ear canal wall, or does not cause allergic reactions) may not be optimal for other parameters such as acoustic reflectivity or membrane permeability. Sound reflectivity affects sound isolation while membrane permeability relates to how long an acoustic seal can be maintained. In at least one exemplary embodiment, a barrier is provided that can improve acoustic reflectivity, permeability of the medium, or both.

In a non-limiting example, a balloon comprising silicone has been shown to be comfortable in subjective testing and is biologically compatible with a large segment of the population. A limitation of silicone is its high permeability to gas (e.g. air). An expanded silicone balloon having a thin wall membrane will not stay inflated for an extended period of time. Maintaining an acoustic seal and stability of an earpiece for an extended period of time is desirable because these devices are intended to be used for periods such as an eight hour work shift. An alternative is to use a medium such as a liquid or gel to expand the balloon, which will not leak through the thin membrane. In practice, a liquid or gel could pose different problems. For example, the system could not work in cold temperature conditions due to freezing of the liquid or discomfort due to the difficulty in warming the liquid to body temperature.

A two-balloon system enhances the performance of the expandable element. The balloon within a balloon system as described hereinbelow can comprise a combination of variable volume balloon and fixed volume balloon or they can be the same type. A balloon 1206 is an outer balloon having a membrane that contacts and forms an acoustic seal with an ear canal wall. A balloon 1204 is internal to balloon 1206. In at least one exemplary embodiment, balloons 1204 and 1206 are attached to support structure 1102. The medium 1202 is provided to balloon 1204. Balloon 1204 expands when filled with the medium 1202 and also expands the overlying membrane of balloon 1206. In one example, the membrane material of balloon 1204 is selected to have a low permeability to the medium 1202 such that the acoustic seal is maintained over an extended period of time. In other words, the membrane of balloon 1204 is a barrier for the medium 1202. The membrane of balloon 1204 is between the medium 1202 and the membrane of balloon 1206. For example, nylon 6 used for balloon 1204 has permeability approximately 10,000 times lower than silicone. Alternatively, a material such as urethane has a lower permeability than silicone. Thus, a medium such as air will have an extremely low leakage rate through nylon 6 and the acoustic seal can be maintained for an extended period of time. In another example, the membrane material can also be selected to have a high acoustic reflectivity to further reflect sound that penetrates the membrane of balloon 1206. Sound penetrating the membrane of balloon 1206 is reflected away from the sealed ear canal volume to improve isolation or reduce the occlusion effect (for reflecting bodily conducted sound). Alternatively, an internal or external surface of the membrane of balloon 1204 can be coated with an acoustically reflective material that would also function to increase sound isolation from the ambient environment as well as reducing the occlusion effect. The internal or external surface of balloon 1204 is isolated from contacting the ear canal wall by the membrane material of balloon 1206.

In at least one exemplary embodiment, a second medium is placed between the membranes of balloons 1204 and 1206 as a further barrier. In a non-limiting example, air is used to expand balloon 1204. A second medium such as water is placed between the membranes of 1204 and 1206 to reduce leakage of the air through the membrane of balloon 1204. For example, the membranes of balloons 1204 and 1206 comprise silicone. Air used to expand balloon 1204 would normally diffuse through the silicone membrane reducing the air volume, which at some point would break the acoustic seal in the ear canal. In other words, additional air would have to be added to balloon 1204 periodically to make up for the leakage through membranes of balloons 1204 and 1206. A liquid medium such as water in a volume 1208 between the membranes of balloons reduces the diffusion of air through the membrane of balloon 1204. The air is not readily soluble into the water that is in contact with the membrane surface of balloon 1204. Thus, the liquid medium acts as a barrier to the air trying to diffuse through the membrane of balloon 1204. As stated, more than one medium can be introduced into expanding device 1200 to enhance the performance and operation of the device.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions of the relevant exemplary embodiments. Thus, the description of the invention is merely exemplary in nature and, thus, variations that do not depart from the gist of the invention are intended to be within the scope of the exemplary embodiments of the present invention. Such variations are not to be regarded as a departure from the spirit and scope of the present invention.

What is claimed is:

1. An expandable device configured to occlude an ear canal comprising:
    a support structure having a first input port and a second input port;
    a deformable element operatively connected to at least a portion of the support structure, the first input port of the support structure being pneumatically coupled to the deformable element, the deformable element including a further port coupled to an ambient environment;
    a valve disposed in and operatively connected to a flexible housing, the valve being operatively connected to the first input port by a channel, the valve being configured to open responsive to deformation of the flexible housing; and
    a membrane having a distal end and a proximal end, where the distal end and the proximal end are circumferentially attached to the support structure forming an expandable element, the expandable element being coupled to the second input port of the support structure, where the expandable element is configured to be in an un-expanded state and an expanded state, such that, in the un-expanded state, the expandable element is adjacent to the support structure, an extent of the expandable element in the un-expanded state being configured to minimize an insert profile of the expandable device,
    where reducing an internal volume of the deformable element while the further port of the deformable element is closed delivers a medium in the internal volume through the valve to expand the expandable element, and
    where the deformable element returns to a quiescent volume when a reducing force is removed from the deformable element and the further port of the deformable element is open.

2. The expandable device of claim 1 where the insert profile of the expandable device is approximately a maximum width of the support structure plus twice a thickness of the membrane.

3. The expandable device of claim 2 where the insert profile of the expandable device into the ear canal is less than 4.0 millimeters.

4. The expandable device of claim 1 where the medium includes at least one of a gas, a liquid, or a gel.

5. The expandable device of claim 4 where the membrane comprises silicone, where the medium comprises the gas, and where a gas barrier is provided between the membrane and the gas for preventing gas leakage from the expandable device.

6. The expandable device of claim 1 where the membrane in the expanded state forms an acoustic seal with a wall of the ear canal where the membrane is under tensile stress.

7. The expandable device of claim 6 where the membrane in the expanded state has an internal pressure approximately 1 atmosphere or greater.

8. The expandable device of claim 7 where the membrane in the expanded state has an internal pressure approximately less than 1.3 atmospheres.

9. The expandable device of claim 1 further including a flange to limit an insertion depth of the expandable device.

10. The expandable device of claim 9 where the flange at least partially seals an ear canal opening to limit sound from entering the ear canal.

11. The expandable device of claim 1 further including additional membranes attached to the support structure forming expandable elements that in the expanded state form an acoustic seal with a wall of the ear canal.

12. The expandable device of claim 1, where:
the membrane includes a first membrane and a second membrane forming respective first and second expandable elements, each expandable element including a balloon, the medium including a first medium and a second medium, and
the second expandable element is disposed within the first expandable element where the second expandable element is filled with the first medium to expand the first and second expandable elements such that the first membrane of the first expandable element forms an acoustic seal with a wall of the ear canal.

13. The expandable device of claim 12 where the second membrane has a lower permeability to the first medium than the first membrane.

14. The expandable device of claim 12, where a region between the first membrane and the second membrane is filled with the second medium, where the second medium is less permeable to the first medium than at least one of the first and second membranes.

15. The expandable device of claim 12 where the first medium is a gas and where the second medium is a liquid disposed between the first and second membranes of the first and second expandable elements.

16. The expandable device of claim 1 further including a barrier between the membrane and the medium for expanding the membrane, the barrier configured to reduce leakage of the medium through the membrane.

17. An expandable device configured to increase an acoustic isolation of an ear canal volume comprising:
a support structure having a first input port and a second input port;
a deformable element operatively connected to at least a portion of the support structure, the first input port of the support structure being pneumatically coupled to the deformable element, the deformable element including a further port coupled to an ambient environment;
a valve disposed in and operatively connected to a flexible housing, the valve being operatively connected to the first input port by a channel, the valve being configured to open responsive to deformation of the flexible housing; and
an expandable element coupled to the second input port of the support structure, the expandable element configured to be inserted into the ear canal volume,
where reducing an internal volume of the deformable element while the further port of the deformable element is closed delivers a medium in the internal volume through the valve to expand the expandable element, and
where the deformable element returns to a quiescent volume when a reducing force is removed from the deformable element and the further port of the deformable element is open.

18. The expandable device according to claim 17, further comprising a stop barrier, where the stop barrier is coupled to the support structure, where the stop barrier facilitates limiting a depth of insertion of the expandable device into the ear canal volume.

19. The expandable device of claim 17 where the medium in the expandable element is transferred through the valve when the valve is opened by deforming the flexible housing and the further port of the deformable element is open.

* * * * *